United States Patent [19]

Grollier et al.

[11] Patent Number: 4,957,732
[45] Date of Patent: Sep. 18, 1990

[54] SHAVING COMPOSITION FOR THE SKIN BASED ON POLYORGANO-SILOXANES CONTAINING AN ACYLOXYALKYL GROUP AND PROCESS FOR USE

[75] Inventors: Jean F. Grollier, Paris; Alain Caudet, Boulogne-Billancourt, both of France

[73] Assignee: L'Oreal, Paris, France

[21] Appl. No.: 458,236

[22] Filed: Dec. 28, 1989

[30] Foreign Application Priority Data

Dec. 29, 1988 [FR] France .................. 8817433

[51] Int. Cl.$^5$ .............................................. A61K 7/15
[52] U.S. Cl. ........................................ 424/73; 424/47; 514/772
[58] Field of Search .................. 424/47, 73; 514/772

[56] References Cited

FOREIGN PATENT DOCUMENTS 331915 9/1989 European Pat. Off. .
2126111 6/1987 Japan .

Primary Examiner—Merrell C. Cashion, Jr.
Assistant Examiner—Susan S. Rucker
Attorney, Agent, or Firm—Marshall, O'Toole, Gerstein, Murray & Bicknell

[57] ABSTRACT

Shaving composition for the skin containing a polyorganosiloxane selected from:
(i) compounds of formula (I):

$$(R)_3Si-O-\underset{\underset{OCOR''}{|}}{\underset{R_1}{\overset{R'}{\underset{|}{Si}}}}\!\!\!\!\overline{)_p}-O-\underset{\underset{OH}{|}}{\underset{R_1}{\overset{R'}{\underset{|}{Si}}}}\!\!\!\!\overline{)_q}-O-\underset{R'}{\overset{R'}{\underset{|}{Si}}}\!\!\!\!\overline{)_r}OSi(R)_3 \quad (I)$$

where:
R denotes methyl, phenyl, OCOR'', hydroxyl;
R' denotes methyl, phenyl;
$R_1$ denotes alkylene of the hydrocarbon ($C_2$-$C_{18}$) type;
R'' denotes alkyl, alkenyl;
r a number between 1 and 120 inclusive;
p a number between 1 and 30;
q is 0 or less than 0.5 p; p+q between 1 and 30;
(ii) compounds of formula (II):

$$\left[\underset{R'}{\overset{R'}{\underset{|}{Si}}}\!\!-\!\!O\right]_s\left[\underset{\underset{OCOR''}{|}}{\underset{R_1}{\overset{R'}{\underset{|}{Si}}}}\!\!-\!\!O\right]_t\left[\underset{\underset{OH}{|}}{\underset{R_1}{\overset{R'}{\underset{|}{Si}}}}\!\!-\!\!O\right]_u \quad (II)$$

where:
s is between 0 and 20;
t is between 1 and 20;
u is 0 or less than 0.5 t; t+u between 1 and 20.

14 Claims, No Drawings

SHAVING COMPOSITION FOR THE SKIN BASED ON POLYORGANO-SILOXANES CONTAINING AN ACYLOXYALKYL GROUP AND PROCESS FOR USE

The present invention relates to new compositions intended for shaving of the skin, based on polyorganosiloxanes containing an acyloxyalkyl group, and to a process for using them.

Some polyorganosiloxanes are well known in the field of shaving compositions, and are used in formulations for shaving cream, pre-shave lotions and shaving foams. They are chiefly volatile silicones such as polydimethylsiloxane or "dimethicone", or polydimethylcyclosiloxane or "cyclomethicone".

These silicones, used in shaving compositions, have the function of alleviating shaving rash as a result of their lubricating power, of making the skin softer and more satiny and of making the compositions containing them rather agreeable to use.

However, these silicones are also known for their antifoam property, and are difficult to use in shaving foams packaged as aerosols. When these silicones permit foam formation, the foam generally varies greatly in quality and stability according to the extent of filling of the aerosol container.

The applicants discovered, surprisingly, that the use of polyorganosiloxanes containing an acyloxyalkyl group in shaving compositions enabled a substantial improvement to be obtained in the smoothness and softness of these compositions, in addition to the properties stated above for silicones.

The applicants also discovered that the use of these polyorganosiloxanes containing an acyloxyalkyl group in shaving foams enabled the latter to preserve the qualities mentioned above and their stability during the gradual emptying of the aerosol container.

Finally, the applicants discovered that the compositions according to the invention, containing polyorganosiloxanes containing an acyloxyalkyl group, improved the cutting of the hairs during shaving, were removed exceptionally well from both the skin and razor blades on rinsing with water, and rapidly left the skin clean and satiny.

A subject of the invention consists of the compositions intended for shaving of the skin, containing polyorganosiloxanes containing an acyloxyalkyl group.

The subject of the invention is also a process for shaving the skin employing these compositions.

Other subjects of the invention will become apparent on reading the description and the examples which follow.

The subject of the present invention is hence a composition intended for shaving of the skin, containing, in a cosmetically acceptable medium, a foaming agent and at least one polyorganosiloxane containing an acyloxyalkyl group, selected from:

(i) linear compounds corresponding to the following average formula (I):

$$(R)_3Si+O-Si+_r(-O-Si+_p(-O-Si+_q-OSi(R)_3$$

in which:
the radicals R, which may be identical or different, are selected from methyl, phenyl, OCOR" and hydroxyl radicals; only one of the radicals R per silicon atom can be OH;
the radicals R', which may be identical or different, are selected from methyl and phenyl radicals; at least 60 mol % of all the radicals R and R' is methyl;
$R_1$ is a divalent linear or branched alkylene group of the hydrocarbon type containing from 2 to 18, and preferably from 2 to 6, carbon atoms, and more especially a trimethylene $-(CH_2)_3-$ and 2-methyltrimethylene $$-CH_2-CH-CH_2- \text{ chain;} \\ | \\ CH_3$$

R" is a $C_8-C_{20}$ alkenyl or alkyl radical;
r is a number between 1 and 120 inclusive;
p is a number between 1 and 30; and
q is equal to 0 or is a number not exceeding 0.5 p, the sum p+q being between 1 and 30; and (ii) cyclic compounds corresponding to the following average formula:

(II)

in which:
R', R" and $R_1$ have the same meaning as stated above;
s is a number between 0 and 20;
t is a number between 1 and 20; and
u is equal to 0 or is equal to a number not exceeding 0.5 t, the sum t+u being between 1 and 20, the sum s+t+u being not less than 3.

The polyorganosiloxanes containing a linear acyloxyalkyl group of the formula (I) can optionally contain $$CH_3Si-OH \\ | \\ O2/2$$

groups, present in proportions not exceeding 15% of the sum p+q+r.

Among especially preferred compounds used according to the invention, the compounds of the formula (I) or (II) in which:
R denotes a methyl;
R' denotes a methyl;
$R_1$ denotes $-(CH_2)_3-$;
R" denotes $C_{12}H_{25}$, $C_{14}H_{29}$, $C_{16}H_{33}$, $C_{18}H_{37}$, oleyl;
r is between 1 and 30;
p is between 5 and 16;
q is between 0.5 and 4; and
s+t+u is between 3 and 10 inclusive; may be used.

Compounds of average formulae (I) and (II) are obtained by esterification of diorganopolysiloxanes containing a hydroxyalkyl group, of average formulae (III) and (IV):

$$(R_2)_3-Si-O-\underset{\underset{OH}{\underset{|}{R_1}}}{\underset{|}{Si}}\!\!\!\overset{}{{}_{\overline{a}}}\!\!(-O-\underset{\underset{R'}{|}}{\underset{|}{Si}}\!\!){}_{\overline{b}}OSi(R_2)_3 \quad \text{(III)}$$

in which

R' and $R_1$ have the same meaning as stated above;

$R_2$ represents a methyl, phenyl or hydroxyl radical; only one of the radicals $R_2$ per silicon atom can be hydroxyl;

at least 60% of all the radicals $R_2$ and R' is methyl; and a is between 1 and 30 and b is between 1 and 20;

it being possible for the compounds of formula (III) to contain $$CH_3-\underset{\underset{O_{2/2}}{\diagdown}}{Si}-OH$$

units, in proportions not exceeding 15% of the sum a+b;

$$\left[\underset{\underset{R'}{|}}{\underset{|}{Si}}-O\right]_c \left[\underset{\underset{OH}{|}}{\underset{|}{Si}}-O\right]_d \quad \text{(IV)}$$

in which R' and $R_1$ have the same meanings as in the formula (II) shown above, c is between 0 and 20 and d is between 1 and 20, the sum c+d being not less than 3.

The esterification is performed in a known manner, with an acid R″COOH or the acid anhydride, at a temperature of between 100° and 250° C., optionally in the presence of a catalyst such as aluminium chloride or zinc chloride or of a strong acid such as hydrochloric acid or sulphuric acid.

It is also possible to perform a transesterification, by heating a methyl ester of the formula R″COOCH$_3$ and a diorganopolysiloxane of the formula (III) or (IV) to 100°-150° C. in the presence of an acidic catalyst such as para-toluenesulphonic acid or an acidic earth of the montmorillonite type (KATALYSATOR KSF/O, sold by SUD-CHEMIE - A.G. MUNCHEN).

The products of formulae (III) and (IV) are known per se, and may be prepared according to known processes of the prior art, such as those described in U.S. Pat. Nos. 4,160,775 and 2,970,150 or in Patent Application FR No. 85/16334.

To prepare the products of formulae (III) and (IV), it is possible, for example, to use as a starting hydrogenopolysiloxane the copolymers of formula (V) or (VI):

$$(R_2)_3-Si-O-\underset{\underset{H}{|}}{\underset{|}{Si}}\!\!\!\overset{}{{}_{\overline{a}}}\!(-O-\underset{\underset{R'}{|}}{\underset{|}{Si}}\!\!){}_{\overline{b}}OSi(R_2)_3 \quad \text{(V)}$$

$$\left[\underset{\underset{R'}{|}}{\underset{|}{Si}}-O\right]_c \left[\underset{\underset{H}{|}}{\underset{|}{Si}}-O\right]_d \quad \text{(VI)}$$

in which:

$R_2$, a, b and R' have the same meanings as in the formula (III), and

R', c and d have the same meanings as in the formula (IV).

The products of formulae (V) and (VI) are well known in the silicone industry and are generally available on the market.

The products of formulae (V) and (VI) are reacted with an alkenically unsaturated alcohol of formula R′$_1$OH, where R′$_1$ is a linear or branched $C_2$-$C_{18}$ alkenyl radical.

Among these alcohols, allyl alcohol or methallyl alcohol is used more especially.

As a hydrosilylation catalyst for reacting the unsaturated alcohols with the hydrogenopolysiloxane of the formula (V) or (VI), it is possible to use known hydrosilylation catalysts, in particular the platinum complexes described in U.S. Pat. Nos. 3,715,334, 3,775,452 and 3,814,730; and the platinum/olefin complexes described in U.S. Pat. Nos. 3,159,601 and 3,159,662.

The cosmetically acceptable medium according to the present invention is an aqueous medium containing at least one foaming agent.

The foaming agent according to the present invention is selected from synthetic anionic surfactants, or soaps consisting of $C_6$-$C_{20}$ fatty acids neutralized with an alkaline agent such as triethanolamine, potassium hydroxide, sodium hydroxide or mixtures thereof.

The synthetic anionic surfactants are selected from alkali metal or ammonium salts of derivatives containing fatty ($C_{14}$-$C_{22}$) chains of glutamic, isethionic, sulphosuccinic and sulphoacetic acids, and of sarcosine or taurine, and more especially from the N-acylglutamates, alkylisethionates, alkylsulphosuccinates, acylaminopolyethoxysulphosuccinates, alkylsulphoacetates, N-acylsarcosinates and N-methyl-N-acyltaurinates, the alkyl and acyl radicals containing from 14 to 22 carbon atoms.

The fatty acids used according to the present invention preferably consist of mixtures of $C_{16}$-$C_{20}$ fatty acids and $C_6$-$C_{20}$ fatty acids, and in particular mixtures of stearic acid and coconut fatty acids or of stearic acid and myristic acid or alternatively stearic acid and lauric acid.

The proportion of $C_{16}$-$C_{20}$ fatty acids in soap is between 40 and 90%, preferably between 75 and 90%, by weight relative to the total weight of the quantity of soap; and that of $C_6$-$C_{20}$ fatty acids in soap is between 10 and 60%, and preferably between 10 and 25%, by weight relative to the total weight of the quantity of soap.

Other foaming agents may be used in combination with the fatty acid soaps or the foaming anionic surfactants defined above, such as, for example, nonionic or amphoteric surfactants or anionic surfactants different from those mentioned above, or polymers such as polyvinyl alcohol.

Preferred compositions according to the invention contain from 10 to 85% by weight of water, and from 0.5 to 80% by weight of soap consisting of $C_6$–$C_{20}$ fatty acids neutralized with an alkaline agent, or of anionic surfactant as defined above.

The compositions for shaving the skin according to the invention contain, in the cosmetically acceptable medium defined above, a polyorganosiloxane containing an acyloxyalkyl group of the formula (I) or (II) in concentrations of between 0.2 and 3% by weight, and preferably between 0.5 and 2% by weight, relative to the total weight of the composition.

These compositions may be presented in the form of creams, gels, self-foaming gels, solid cakes and, more especially, aerosol foams.

The shaving compositions according to the invention may be packaged as aerosols and distributed in the form of foams or self-foaming gels.

In this case, the composition is used in the presence of a propellent gas, selected from volatile hydrocarbons such as n-butane, isobutane and propane, of which a ternary mixture of n-butane, isobutane and propane sold, for example, by the company ELF AQUITAINE under the name AEROGAZ 3,2 N is more especially preferred, or partially or completely fluorinated hydrocarbons including, more especially, monofluorotrichloromethane, dichlorodifluoromethane (F12) and 1,2-dichloro-1,1,2,2-tetrafluoroethane (F114), used alone or in combination; chlorinated and/or fluorinated hydrocarbons of this type are sold under the name of Fréon or Dymel by the company DU PONT DE NEMOURS. It is also possible to use as a propellant mixtures of these volatile hydrocarbons with chlorinated and/or fluorinated hydrocarbons, such as, for example, a mixture of n-butane, isobutane, propane and monofluorotrichloromethane, or propellants such as nitrous oxide, carbon dioxide or dimethyl ether.

More especially preferred shaving compositions according to the invention are represented by aerosol foams containing from 75 to 85% by weight of water, from 0.5 to 15% by weight of soap or anionic surfactant as defined above, from 0.2 to 3% by weight of a polyorganosiloxane of the formula (I) or (II) and from 2 to 15%, and more especially from 3 to 10%, by weight of a propellent agent.

The compositions according to the invention can contain, in addition to the polyorganosiloxane of the formula (I) or (II), adjuvants customarily used in the field of shaving compositions, such as moisturizing agents selected from sorbitol and glycerol, transparency agents also playing the part of a solvent, such as glycols, for example propylene glycol or ethylene glycol, film-forming agents, emollients such as, for example, lanolin derivatives or cationic polymers or polyethylene glycols, skin treatment agents such as healing agents, mineral oils, fatty alcohols, polymers, thickeners, stabilizing agents such as, for example, ethanolamides, soothing agents such as allantoin, camphor and menthol, anionic surfactants other than soaps and those mentioned above, nonionic or amphoteric surfactants or mixtures thereof, colourings, preservatives, antioxidants and fragrances.

The process for shaving the skin according to the present invention consists essentially in applying a composition as defined above to the skin, in shaving the latter by means of a mechanical razor and in following this by rinsing with water.

The examples which follow are designed to give a better illustration of the invention without, however, limiting the latter.

PREPARATION EXAMPLES

EXAMPLE A

Preparation of a compound of average formula (I) in which:

$R = R' = CH_3$, $R_1 = -(CH_2)_3-$
$p = 7.9$
$q = 1.4$
$r = 9.3$
$R'' =$ mixture of $C_{16}H_{33}$ and $C_{18}H_{37}$ radicals.

This compound contains on average approximately two

units

A 3-liter three-necked round-bottomed flask, equipped with a stirrer, provided with a heating device and a reflux condenser and swept with a stream of nitrogen by bubbling through the reaction medium, is charged with 800 g of a polydimethylsiloxane oil containing a γ-hydroxypropyl group (obtained by a hydrosilylation reaction of allyl alcohol with a polydimethylpolymethylhydrogenosiloxane oil in the presence of a platinum-based catalyst) of average molecular structure, determined by $^{29}Si$ NMR analysis, corresponding to the average formula (III) in which:

$R_2 = R' = CH_3$
$R_1 = -(CH_2)_3-$
$a = 6.8$
$b = 6.8$ and containing on average one

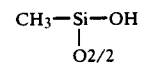

unit, assaying at 459.5 meq/100 g of propyl alcohol groups, and 1207 g of a cut of fatty esters $R''CO_2Me$, $R''$ having the composition:

| | |
|---|---|
| $C_{14}H_{29}$ | 0.5 |
| $C_{16}H_{33}$ | 37.0 |
| $C_{18}H_{37}$ | 61.0 |
| $C_{20}H_{41}$ | 1.5 |
| | 100% by weight |

The medium is brought by heating to 120° C. When the temperature is reached, 6.02 g of paratoluenesulphonic acid monohydrate ($CH_3C_6H_4SO_3H.H_2O$) are added.

The reaction is performed with stirring for 17 hours. At the end of the reaction, 500 ml of hexane are added to the reaction medium and removal of the acidic catalyst is then performed by washing and neutralization with aqueous $NaHCO_3$.

The hexane phase is dried over $Na_2SO_4$ and filtered. 1822.6 g of a clear amber-coloured oil in which 85% of the alcohol groups are converted to a fatty ester group are obtained after removal of the hexane by distillation at 110° C. at 1.33 kPa for 3 hours. The oil assumes the appearance of a wax on cooling to room temperature.

$^{29}$Si NMR analysis indicates the structure mentioned above.

The residual content of propyl alcohol groups is 37 meq/100 g, and of methyl $C_{16}+C_{18}$ fatty esters 20% by weight.

EXAMPLE B

The same operations are performed as in Example A, except that 250 g of the γ-hydroxypropyl oil used above and 370.5 g of the fatty ester cut are introduced. When the medium is homogeneous after heating to 110° C., 12.41 g of a montmorillonite type KATALYSATOR KSF/O acidic earth are introduced.

After 17 hours' reaction, the reaction medium is filtered while hot (80° C.), and 545.8 g of oil are obtained, in which 85% of the alcohol groups are converted to a fatty ester group.

The molecular structure, determined by $^{29}$Si NMR analysis, corresponds to the average formula (I) in which:

$R = R' = CH_3$; $R_1 = -(CH_2)_3-$
$p = 14.8$
$q = 2.6$
$r = 17.4$
$R'' =$ mixture of $C_{16}H_{33}$ and $C_{18}H_{37}$ radicals.

This compound contains, on average, approximately three

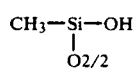

units.

The residual content of methyl $C_{16}+C_{18}$ fatty esters is 18 7% by weight.

COMPOSITION EXAMPLES

EXAMPLE 1

An aerosol shaving foam of the following composition is prepared:

| | |
|---|---|
| Stearic acid | 8.0 g |
| Coconut fatty acid | 1.0 g |
| Sodium hydroxide | 0.5 g |
| Triethanolamine | 3.0 g |
| Diorganopolysiloxane of Example A | 1.5 g |
| Glycerol | 2.5 g |
| Amphoteric surfactant known as "Coco-amphocarboxyglycinate" (in the CTFA, 3rd edition, 1982), sold by the company MIRANOL under the name MIRANOL C$_2$M conc., in aqueous solution containing 38% of active substance | 0.1 g AS |
| Polyethylene glycol, sold by the company UNION CARBIDE under the name Polyox coagulant grade | 0.05 g |
| Polyoxyethylenated sorbitan monolaurate containing 20 moles of ethylene oxide, sold by the company ATLAS under the name TWEEN 20 | 0.3 g |
| Fragrance qs | |
| Water | qs 100.0 g |
| Aerosol packaging: | |
| Above composition | 97.0 g |
| Propellant: | |
| Ternary mixture of n-butane, isobutane > 55% and propane, sold by the company ELF AQUITAINE under the name AEROGAZ 3,2 N | 3.0 g |
| Total | 100.0 g |

EXAMPLE 2

An aerosol shaving foam of the following composition is prepared:

| | |
|---|---|
| Stearic acid | 5.5 g |
| Myristic acid | 1.2 g |
| Potassium hydroxide | 0.4 g |
| Triethanolamine | 3.3 g |
| Glycerol | 5.0 g |
| Lanolic acid | 0.5 g |
| Polyvinylpyrrolidone K 30, sold by the company GAF | 1.0 g |
| Diorganopolysiloxane of Example A | 1.0 g |
| Myristate of a mixture of isopropanol-amines, sold by the company AMERCHOL under the name LANAMINE | 2.0 g |
| Polyoxyethylenated sorbitan monolaurate containing 20 moles of ethylene oxide, sold by the company ATLAS under the name TWEEN 20 | 0.5 g |
| Fragrance qs | |
| Water | qs 100.0 g |
| Aerosol packaging: | |
| Above composition | 90.0 g |
| Propellant: Freons 12/114 (53/47) | 10.0 g |

EXAMPLE 3

An aerosol shaving foam of the following composition is prepared:

| | |
|---|---|
| Stearic acid | 6.0 g |
| Coconut fatty acid | 0.75 g |
| Sodium hydroxide | 0.45 g |
| Triethanolamine | 2.25 g |
| Diorganopolysiloxane of Example A | 2.0 g |
| Sorbitol | 5.0 g |
| Propylene glycol | 2.5 g |
| Dimethyldiallylammonium/acrylamide copolymer, sold by the company MERCK in aqueous solution containing 8% of active substance (AS) under the name MERQUAT S | 0.5 g AS |
| Fragrance qs | |
| Water qs | qs 100.0 g |
| Aerosol packaging: | |
| Above composition | 95.0 g |
| Ternary mixture of n-butane, isobutane > 55% and propane, sold by the company ELF AQUITAINE under the name AEROGAZ 3,2 N | 5.0 g |
| Total | 100.0 g |

EXAMPLE 4

A self-foaming shaving gel of the following composition is prepared:

| | |
|---|---|
| Stearic acid | 5.0 g |
| Palmitic acid | 5.0 g |
| Triethanolamine | 5.55 g |
| Polyethylene glycol ether (20 EO) of oleyl alcohol, sold by the company ICI under the name BRIJ 98 | 2.0 g |
| Hydroxyethylcellulose, sold by the company UNION CARBIDE under the name CELLOSIZE PCG 10 | 1.35 g |
| Sorbitol | 2.0 g |
| Diorganopolysiloxane of Example A | 2.0 g |
| Polyethylene glycol, sold by the company UNION CARBIDE under the name POLYOX WSR 205 | 0.5 g |
| Fragrance, colouring qs | |

| | |
|---|---|
| Water qs | qs 100.0 g |

96 g of this composition are introduced with 2.5 g of isopentane and 1.5 g of isobutane into the central part of a double-walled aerosol can, the inner wall of which consists of an impermeable compressible membrane separating the propellant (outer jacket) from the gelled self-foaming composition (central part).

After the valve is fitted, the aerosol can be pressurized by introducing 10% of a ternary mixture of n-butane, isobutane>55% and propane, sold by the company ELF AQUITAINE under the same AEROGAZ 3,2 N, into the jacket.

EXAMPLE 5

An aerosol shaving foam of the following composition is prepared:

| | |
|---|---|
| Stearic acid | 8.3 g |
| Coconut fatty acid | 0.7 g |
| Potassium hydroxide | 0.9 g |
| Triethanolamine | 3.1 g |
| Glycerol | 2.5 g |
| Polyoxyethylenated sorbitan monolaurate containing 20 moles of ethylene oxide, sold by the company ATLAS under the name TWEEN 20 | 1.0 g |
| Myristate of a mixture of isopropanol amines, sold by the company AMERCHOL under the name LANAMINE | 2.0 g |
| Diorganopolysiloxane of Example B | 2.0 g |
| Fragrance qs | |
| Water qs | qs 100.0 g |
| Aerosol packaging: | |
| Above composition | 96.7 g |
| Propellant: | |
| Ternary mixture of n-butane, isobutane > 55% and propane, sold by the company ELF AQUITAINE under the name AEROGAZ 3,2 N | 3.3 g |
| Total | 100.0 g |

EXAMPLE 6

A shaving foam of the following composition is prepared:

Monosodium salt of the glutamic acid derivative of formula:

| | |
|---|---|
| HOOC—CH$_2$—CH$_2$—CH—COONa<br>                                       \|<br>                                  NH—COR<br>where R is a mixture of tallow fatty acid-derived C$_{14}$-C$_{22}$ hydrogenated alkyl and/or alkenyl radicals, sold by the company AJINOMOTO under the name ACYLGLUTAMATE HS 11 | 3.0 g |
| Disodium salt of the glutamic acid derivative of the above formula, sold by the company AJINOMOTO under the name ACYLGLUTAMATE HS 21 | 3.5 g |
| Glycerol | 4.0 g |
| Lanolic acid | 1.0 g |
| Amphoteric surfactant known as "Cocoamphocarboxyglycinate" (CTFA, 3rd edition, 1982), sold by the company MIRANOL under the name MIRANOL C2M conc., in aqueous solution containing 38% of active substance AS | 1.0 g AS |
| Hydroxyethylcellulose, sold by the company UNION CARBIDE under the name CELLOSIZE PCG 10 | 0.2 g |
| Polyethylene glycol, sold by the company UNION CARBIDE under the name POLYOX WSR 205 | 0.5 g |
| Diorganopolysiloxane of Example A | 1.0 g |
| Fragrance qs | |
| Water qs | 100.0 g |
| Aerosol packaging: | |
| Above composition | 96.0 g |
| Propellant: | |
| Ternary mixture of n-butane, isobutane > 55% and propane, sold by the company ELF AQUITAINE under the name AEROGAZ 3,2 N | 4.0 g |
| Total | 100.0 g |

EXAMPLE 7

A shaving foam of the following composition is prepared:

| | |
|---|---|
| Oleamidopolyethylene glycol/disodium 2-sulphosuccinate, sold by the company HENKEL under the name STANDAPOL SH 100, at a concentration of 30% of active substance | 7.5 g AS |
| Sorbitol containing 70% AS | 5.0 g AS |
| Hydroxyethylcellulose, sold by the company UNION CARBIDE under the name CELLOSIZE PCG 10 | 0.8 g |
| Diorganopolysiloxane of Example A | 1.5 g |
| Fragrance qs | |
| Water qs | qs 100.0 g |
| Aerosol packaging: | |
| Above composition | 95.0 g |
| Propellant: isobutane | 5.0 g |
| Total | 100.0 g |

We claim:

1. Composition intended for shaving of the skin, characterized in that it contains, in a cosmetically acceptable medium including a foaming agent, a polyorganosiloxane containing an acyloxyalkyl group, selected from:

(i) linear compounds corresponding to the following average formula (I):

$$(R)_3Si\text{-}(O\text{-}Si\underset{\underset{OCOR''}{|}}{\overset{\overset{R'}{|}}{|}}\text{)}_p\text{-}(O\text{-}Si\underset{\underset{OH}{|}}{\overset{\overset{R'}{|}}{|}}\text{)}_q\text{-}(O\text{-}Si\underset{\underset{R'}{|}}{\overset{\overset{R'}{|}}{|}}\text{)}_r\text{-}OSi(R)_3 \qquad (I)$$

in which:

the radicals R, which may be identical or different, are selected from methyl, phenyl, OCOR" and hydroxyl radicals; only one of the radicals R per silicon atom can be OH;

the radicals R', which may be identical or different, are selected from methyl and phenyl radicals; at least 60 mol % of all the radicals R and R' is methyl;

R$_1$ represents a divalent linear or branched alkylene group of the hydrocarbon type containing from 2 to 18 carbon atoms;

R" is a C$_8$-C$_{20}$ alkenyl or alkyl radical;

r is a number between 1 and 120 inclusive;

p is a number between 1 and 30; and q is equal to 0 or is a number not exceeding 0.5 p, the sum p+q being between 1 and 30;

it being possible for the compounds of formula (I) optionally to contain

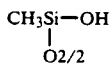

groups, present in proportions not exceeding 15% of the sum p+q+r; and (ii) cyclic compounds represented by the following average formula (II):

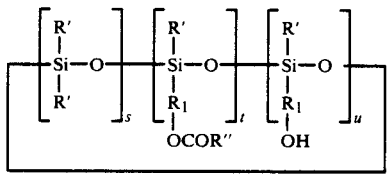

in which:
R', R" and $R_1$ have the same meaning as in the formula (I);
s is a number between 0 and 20;
t is a number between 1 and 20; and
u is equal to 0 or is equal to a number not exceeding 0.5 t, the sum t+u being between 1 and 20;
the sum s+t+u being not less than 3.

2. Composition according to claim 1, characterized in that, in the compounds of formula (I) or (II), $R_1$ represents a divalent linear or branched alkylene group of the hydrocarbon type containing from 2 to 6 carbon atoms.

3. Composition according to claim 1, characterized in that, in the compounds of formula (I) or (II), R represents a methyl radical, R' represents a methyl radical, $R_1$ represents a trimethylene radical, R" denotes $C_{12}H_{25}$, $C_{14}H_{29}$, $C_{16}H_{33}$, $C_{18}H_{37}$, oleyl groups, r is between 1 and 30, p is between 5 and 16, q is between 0.5 and 4 and s+t+u is between 3 and 10 inclusive.

4. Composition according to claim 1 characterized in that it contains, in a cosmetically acceptable medium including a foaming agent, a polyorganosiloxane of formula (I) or (II), in proportions of between 0.2 and 3% by weight, and preferably between 0.5 and 2% by weight, relative to the total weight of the composition.

5. Composition according to claim 1 characterized in that it is presented in the form of creams, gels, self-foaming gels, solid cakes and aerosol foams.

6. Composition according to claim 1 5, characterized in that the cosmetically acceptable medium consists of water and in that the foaming agent is a soap consisting of a $C_6$-$C_{20}$ fatty acid neutralized with an alkaline agent or a synthetic anionic surfactant.

7. Composition according to claim 6, characterized in that the foaming agent is a soap consisting of a mixture of $C_6$-$C_{20}$ fatty acids and $C_{16}$-$C_{20}$ fatty acids, in that the proportion of $C_6$-$C_{20}$ fatty acids is between 10 and 60%, and preferably between 10 and 25%, by weight relative to the total weight of the quantity of soap, and in that the proportion of $C_{16}$-$C_{20}$ fatty acids is between 40 and 90%, and preferably between 75 and 90%, by weight relative to the total weight of the quantity of soap.

8. Composition according to claim 6, characterized in that the anionic surfactant is selected from alkali metal or ammonium salts of derivatives containing fatty ($C_{14}$-$C_{22}$) chains of glutamic, isethionic, sulphosuccinic, and sulphoacetic acids, and of sarcosine or taurine.

9. Composition according to claim 6 characterized in that it contains from 10 to 85% by weight of water and from 0.5 to 80% by weight of said foaming agent.

10. Composition according to claim 1 characterized in that it contains a foaming polymer or a nonionic or amphoteric surfactant or an anionic surfactant different from soaps and from those defined in claim 8.

11. Composition according to claim 1 characterized in that it is packaged as an aerosol in the presence of a propellent gas, so as to form a selffoaming gel or a foam at the time of expulsion.

12. Composition according to claim 11, characterized in that it is presented in the form of an aerosol foam, in that it contains from 75 to 85% by weight of water, 0.5 to 15% by weight of foaming agent as defined in claims 6 to 8, 0.2 to 3% by weight of an organopolysiloxane of formula (I) or (II) and from 2 to 15% by weight of a propellent gas, and preferably 3 to 10% by weight, relative to the total weight of the composition.

13. Composition according to any one of claim 1 characterized in that it contains, in addition, moisturizing agents, transparency agents, film-forming agents, emollients, healing agents, mineral oils, fatty alcohols, polymers, thickeners, stabilizing agents, soothing agents, anionic surfactants other than soaps and those defined in claim 8, nonionic or amphoteric surfactants or mixtures thereof, colourings, preservatives, antioxidants and fragrances.

14. Process for shaving the skin, characterized in that a composition as defined in claim 1 is applied to the skin, in that the skin is shaved by means of a mechanical razor and in that it is rinsed with water.

* * * * *